(12) United States Patent
Enscore et al.

(10) Patent No.: US 6,174,545 B1
(45) Date of Patent: *Jan. 16, 2001

(54) DRUG DELIVERY DEVICES AND PROCESS OF MANUFACTURE

(75) Inventors: David J. Enscore, Sudbury, MA (US); Patricia S. Campbell, Palo Alto, CA (US); Diane Nedberge, Los Altos, CA (US); Richard D. Frame, San Diego, CA (US)

(73) Assignee: Alza Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/243,873

(22) Filed: Feb. 3, 1999

Related U.S. Application Data (63) Continuation of application No. 08/886,960, filed on Jul. 1, 1997, now abandoned.
(60) Provisional application No. 60/021,124, filed on Jul. 3, 1996.

(51) Int. Cl.[7] ........................................... A61F 13/02
(52) U.S. Cl. .................. 424/448; 424/449; 514/691; 514/947; 602/41; 604/289; 604/304; 604/305; 604/307; 604/892.1
(58) Field of Search ................... 424/448, 449; 514/947, 691; 602/41; 604/892.1, 289, 304, 305, 307

(56) References Cited

U.S. PATENT DOCUMENTS

| 3,598,122 | 8/1971 | Zaffaroni | 128/268 |
| 3,598,123 | 8/1971 | Zaffaroni | 128/155 |
| 3,742,951 | 7/1973 | Zaffaroni | 128/268 |
| 3,797,494 | 3/1974 | Zaffaroni | 128/268 |

(List continued on next page.)

FOREIGN PATENT DOCUMENTS

| 63-093714 | 4/1988 | (JP) . |
| WO92/07590 | 5/1992 | (WO) . |
| WO92/20377 | 11/1992 | (WO) . |
| WO94/06383 | 3/1994 | (WO) . |
| WO95/09006 | 4/1995 | (WO) . |
| WO96/19205 | 6/1996 | (WO) . |
| WO 96/35427 | 11/1996 | (WO) . |
| WO 97/10812 | 3/1997 | (WO) . |
| WO97/20550 | 6/1997 | (WO) . |
| WO97/24148 | 7/1997 | (WO) . |

OTHER PUBLICATIONS

Cleary, Gary W., "Topical Drug Bioavailability, Bioequivalence, and Penetration", Ch. 2, pp 17–68, Transdermal Delivery Systems: A Medical Rationale, 1993.

Cleary, Gary W., "Skin Permeation Fundamental and Application", Ch. 11, pp 207–237, Transdermal Drug Delivery, 1993.

Govil, Sharad K., "Drug Delivery Devices Fundamental and Applications", Ch. 13 pp 385–419, Transdermal Drug Delivery Devices, 1988.

Chien, Y.W., S.T.P., Pharma Sciences 1 (1) 5–23 1991, Transdermal Systemic Drug Delivery Recent Development and Future Prospects.

Primary Examiner—S. Mark Clardy
Assistant Examiner—Michael A. Williamson
(74) Attorney, Agent, or Firm—Vandana Date; Owen J. Bates (57) ABSTRACT

An improved process for manufacturing transdermal drug delivery devices and devices made therefrom. The invention provides a heat equilibration process for the manufacture of drug delivery devices which eliminates the need to preload the body contacting layer with a drug. The method has particular application in the manufacture of transdermal drug delivery devices including a drug reservoir comprising drug in excess of saturation.

8 Claims, 3 Drawing Sheets

U.S. PATENT DOCUMENTS

| | | | |
|---|---|---|---|
| 3,854,480 | 12/1974 | Zaffaroni | 128/260 |
| 3,938,515 | 2/1976 | Leeper et al. | 128/260 |
| 4,031,894 | 6/1977 | Urquhart et al. | 128/268 |
| 4,060,084 | 11/1977 | Chandrasekaran et al. | 128/260 |
| 4,144,317 | 3/1979 | Higuchi et al. | 424/21 |
| 4,201,211 | 5/1980 | Chandrasekaran et al. | 128/268 |
| 4,379,454 | 4/1983 | Campbell et al. | 604/897 |
| 4,588,580 | 5/1986 | Gale et al. | 424/21 |
| 4,704,282 | 11/1987 | Campbell et al. | 424/449 |
| 4,725,439 | 2/1988 | Campbell et al. | 424/449 |
| 4,758,434 | 7/1988 | Kydonieus et al. | 424/449 |
| 4,832,953 | 5/1989 | Campbell et al. | 424/448 |
| 4,863,970 | 9/1989 | Patel et al. | 514/784 |
| 4,867,982 | 9/1989 | Campbell et al. | 424/449 |
| 4,908,027 | 3/1990 | Enscore et al. | 424/443 |
| 5,004,610 | 4/1991 | Osborne et al. | 424/448 |
| 5,152,997 | 10/1992 | Ebert et al. | 424/449 |
| 5,164,190 | 11/1992 | Patel et al. | 424/448 |
| 5,223,262 | 6/1993 | Kim et al. | 424/448 |
| 5,344,656 | 9/1994 | Enscore et al. | 424/448 |
| 5,508,038 | 4/1996 | Wang et al. | 424/448 |
| 5,641,504 * | 6/1997 | Lee et al. | 424/447 |

* cited by examiner

DRUG DELIVERY DEVICES AND PROCESS OF MANUFACTURE

RELATED APPLICATIONS

This application is a continuation of application Ser. No. 08/886,960, filed Jul. 1, 1997, now abandoned which claims the priority of U.S. Provisional application Ser. No. 60/021,124 filed on Jul. 3, 1996.

FIELD OF INVENTION

This invention relates to an improved process for the manufacture of drug delivery devices and to drug delivery devices produced thereby. The improvement comprises a heat equilibration process which controls the migration of a drug from the drug reservoir through the adjoining layers of the device. Preferably, this process enables improved control over the concentration of the drug in the body contacting layer, such as the contact adhesive layer of a transdermal device, resulting in greater control of the initial loading dose of drug delivered by such devices. The process has particular application in the manufacture of transdermal drug delivery devices comprising a drug reservoir containing a drug at or above saturation.

BACKGROUND OF THE INVENTION

Transdermal delivery devices for the delivery of a wide variety of drugs have been known for some time. Typical devices range from simple monolithic devices such as disclosed in U.S. Pat. No. 4,758,434, to devices including in-line adhesives and release rate controlling membranes as disclosed in U.S. Pat. Nos. 3,598,122, 3,598,123, 3,742,951, 4,031,894, 4,060,084, 4,144,317, 4,201,211, and 4,379,454, all of which are incorporated herein by reference. Such rate-controlled devices generally comprise a backing layer which is impermeable to the drug, a drug reservoir which can contain a permeation enhancer or permeation enhancer mixture in addition to the drug, a contact adhesive layer, and a rate controlling membrane positioned between the drug reservoir and contact adhesive. The layers are typically laminated or heat sealed together to produce a transdermal device.

It is known in the transdermal art to provide the drug reservoir with an initial amount of drug at a concentration at or above its saturation concentration in the reservoir in order to maintain a unit activity source of the drug so that the delivery of drug from the device will remain substantially constant over the intended delivery period. Subsaturated systems, such as disclosed in U.S. Pat. Nos. 4,379,454, 4,908,027, 5,004,610, and 5,344,656, hereby incorporated in their entirety by reference, are also known in the art.

In addition to providing the drug in the drug reservoir, it is also known to preload the contact adhesive with an amount of the drug. For example, U.S. Pat. Nos. 4,201,211, 4,588,580, and 4,832,953, hereby incorporated in their entirety by reference, disclose transdermal drug delivery devices wherein the contact adhesive layer is prepared by solvent casting a mixture of the drug and adhesive. Typically, the preloaded amount corresponds to the amount necessary to provide an initial loading dose which creates a concentration gradient across skin and saturates the skin binding sites underlying the device with the drug to be delivered. Additionally, U.S. Pat. No. 4,832,953 discloses heating a laminate system comprising a dispersion of a liquid in a non-aqueous matrix in order to prevent formation of a crystalline hydrate.

In addition, Cleary "Transdermal Delivery Systems: A Medical Rationale", *Topical Drug Bioavailability, Bioequivalence, and Penetration*, Plenum Press 1993, pp 17–68, provides additional background information regarding commercially available transdermal drug delivery systems. A reasonably complete summary of the factors involved in percutaneous absorption of drugs may be found in Govil, "Transdermal Drug Delivery Devices", *Drug Delivery Devices*, Marcel Dekker, Inc. 1988, pp 385–419; Chien "Transdermal Systemic Drug Delivery Recent Development and Future Prospects", S.T.P. Pharma Sciences, Vol. 1, No. 1, pp 5–23, 1991; and Cleary "Transdermal Drug Delivery", *Skin Permeation Fundamentals and Application*, pp 207–237, 1993, all of which are incorporated herein by reference.

The transdermal route of parenteral delivery of drugs provides many advantages, and transdermal systems for delivering a wide variety of drugs or other beneficial agents have been described. Steroids including testosterone, for example, have been studied for their suitability for transdermal delivery and transdermal drug delivery systems for delivering testosterone are disclosed in the prior art. Current transdermal testosterone systems can be generally classified as either scrotal or non-scrotal systems. Each has its own advantages and disadvantages.

Scrotal systems such as described in U.S. Pat. Nos. 4,704,282, 4,725,439, and 4,867,982, are more limited as to the available surface area for drug delivery while, on the other hand, they do not require the use of permeation enhancers. Non-scrotal systems such as described in U.S. Pat. Nos. 5,152,997 and 5,164,990, while not as limited in area of application, require the use of multiple permeation enhancers and are thus susceptible to the problems attendant therewith, particularly irritation. Irritation occurs as the skin reacts to topically applied substances, particularly those maintained under occlusion, by blistering or reddening accompanied by unpleasant burning, itching, and stinging sensations. It is desirable to keep the number of possibly irritating substances in a transdermal delivery device to a minimum.

More specifically, U.S. Pat. Nos. 4,704,282, 4,725,439, and 4,867,982, which are hereby incorporated by reference in their entirety, disclose the transdermal administration of testosterone through intact scrotal skin. These patents teach that scrotal skin provides a five fold increase in permeability to testosterone over non-scrotal skin. Testosterone is provided in an ethylene vinyl acetate copolymer matrix and is delivered through scrotal skin without the use of permeation enhancers.

U.S. Pat. Nos. 5,152,997 and 5,164,990, hereby incorporated in their entirety by reference, disclose the transdermal administration of testosterone through areas of intact, non-scrotal skin. The U.S. Pat. No. 5,164,990 patent requires an ethanol carrier and additionally includes a permeation enhancer or permeation enhancer mixture such as glycerol monooleate and methyl laurate in order to deliver therapeutically effective amounts of testosterone through non-scrotal skin.

Additionally, U.S. Pat. No. 5,223,262 discloses a system for transdermally delivering a hydrophobic alkanol soluble active agent to the skin at a constant rate utilizing a lower alkanol penetration enhancer. The system comprises an overlying solvent reservoir containing a lower alkanol solvent and a drug reservoir containing an active agent in aqueous alkanol. The two reservoirs are separated by a one way membrane permeable to the alkanol solvent and substantially impermeable to the active agent and water.

WO 96/35427, hereby incorporated in its entirety by reference, discloses a transdermal therapeutic system for the delivery of testosterone which comprises an alcoholic carrier saturated with testosterone and is free of any permeation enhancers. The release rate of the active agent is regulated by the adhesive layer.

WO 97/10812, hereby incorporated in its entirety by reference, discloses methods for manufacturing transdermal drug delivery systems containing supersaturated drug reservoirs which obtain higher drug fluxes. The method involves heating the drug reservoir components to a predetermined temperature and subsequently cooling the drug reservoir components in order to provide a supersaturated reservoir such that it contains only a single phase of drug and reservoir material.

As noted above, it is often desirable to preload the adhesive with an amount of drug in excess of the saturation concentration and this has been done by premixing the drug into the adhesive. However, the process of premixing a drug into the adhesive layer, though enabling an amount of drug in excess of saturation to be initially added to the adhesive, presents considerable practical problems. The drug must be sent to the adhesive supplier to be mixed with the adhesive and subsequently sent back to the manufacturing site where the device is ultimately manufactured. This requires undesirable shipping, time, and perhaps most significantly, this process requires particular facilities at the site of the adhesive supplier which conform with regulatory demands for the manufacture of drug delivery devices.

DISCLOSURE OF THE INVENTION

According to this invention, we have eliminated the need to premix the body contacting layer of a drug delivery device with the drug, while still producing an end product having suitable amounts of drug in excess of saturation in layers other than the drug reservoir, such as the contact adhesive of a transdermal drug delivery device.

Accordingly, one aspect of the invention is to provide an improved method of providing a drug delivery device with a loading dose.

Another aspect of the invention is to provide an improved process of manufacturing drug delivery devices whereby a desired amount of drug may be provided in the various layers of the drug delivery device and to devices made therefrom.

Another aspect of the invention is to eliminate the need to preload the contact adhesive of a transdermal drug delivery device with the drug in order to obtain an end product having an amount of drug in excess of saturation in the adhesive.

Another aspect of this invention is to provide an improved therapeutic transdermal system for the delivery of testosterone through intact, non-scrotal skin in order to achieve therapeutically effective blood levels of testosterone in a patient.

These and other objects and advantages of this invention will be readily apparent from the following description with reference to the accompanying figures.

BRIEF DESCRIPTION OF THE FIGURES

FIG. 2(*a*) is a cross-sectional view of one embodiment of a transdermal drug delivery device prior to heat equilibration.

FIG. 2(*b*) is a cross-sectional view of one embodiment of a transdermal drug delivery device during heat equilibration.

FIG. 2(*c*) is a cross-sectional view of one embodiment of a transdermal drug delivery device after heat equilibration.

DETAILED DESCRIPTION OF THE INVENTION

As used herein, the term "drug" is to be construed in its broadest sense to mean any material which is intended to produce some biological, beneficial, therapeutic, or other intended effect, such as permeation enhancement, for example, on the organism to which it is applied.

As used herein, the term "excess of saturation" refers to a condition wherein drug exists in both a solid phase representing the excess and a dissolved phase which is at saturation in the carrier.

As used herein, the term "loading dose" refers to the amount of drug present in the adhesive layer or other body contacting layer other than the drug reservoir in excess of the saturation concentration.

As used herein, the term "rapidly cooling" refers to a cooling process which takes place over a period of time which is shorter than the period of time at which the device is maintained at an elevated temperature and preferably to a time period over which there is no subsequent reequilibration of the drug containing layers.

As used herein, the term "substantial portion" refers to at least 60% of the administration period.

As used herein, the term "therapeutically effective" refers to the amount of drug or the rate of drug administration needed to effect the desired therapeutic result.

As used herein, the term "transdermal" refers to the use of skin, mucosa, and/or other body surfaces as a portal for the administration of drugs by topical application of the drug thereto.

According to this invention, it has been discovered that a predetermined amount of a drug can be introduced into layers of a drug delivery device which are initially free of drug in excess of saturation, and the amount thereof effectively controlled, by performing a heat equilibration process wherein the device is subjected to an elevated temperature for a predetermined period of time and thereafter rapidly cooled to ambient conditions. The process enables a greater amount of drug to migrate at a much quicker rate into the layers initially free of drug in excess of saturation, such as the rate control membrane and adhesive layers of a transdermal device, than is possible by simply allowing the device to equilibrate at room temperature. The process also allows the layers initially free of drug in excess of saturation to retain predetermined amounts of drug in excess of saturation, after rapidly cooling to ambient conditions. This process eliminates the need to mix the drug and body contacting layer such as the adhesive layer of a transdermal delivery device at a site other than the location of manufacture of the device in order to provide a desired loading dose in the body contacting layer.

The process of the invention may be practiced so as to provide a desired concentration of any drug in any of the particular layers of the final system by selecting an appropriate drug loading in excess of saturation in one of the layers of the device, usually the drug reservoir, and selecting an appropriate time and temperature at which to conduct the heat equilibration process. The temperature selected for the equilibration process must be below that which causes degradation of the drug(s) or which causes other deleterious effects such as undesirable phase changes in the components of the device and is selected such that the drug remains at least at saturation in the layer at the elevated temperature. Temperatures useful in the present invention range from about 30°–60° C., preferably 35°–45° C. Once the temperature is selected, the time may be varied anywhere from about 8 hours to 3 weeks, depending upon the desired loading dose of drug to be delivered. A preferred range of times useful in the practice of the present invention is between about 1 to 10 days.

After the heating process, the devices are rapidly cooled to ambient conditions. The cooling step is performed such that drug is provided in excess of saturation in the desired layer(s) of the device. Preferably, the cooling process comprises subjecting the devices to a temperature below the elevated temperature for a period of time less than that at which the devices are subjected to the heating process. Preferred temperatures for the rapid cooling are at ambient conditions and preferred cooling times are from 6 hours to 5 days and most preferably from 6 to 36 hours.

This invention finds applicability with any type of drug delivery device which utilizes a loading dose of drug in one of its layers. For example, drug delivery systems such as those disclosed in U.S. Pat. Nos. 3,854,480 and 3,938,515, hereby incorporated in their entirety by reference, may be used in the practice of this invention in order to provide the outer polymeric membrane with a loading dose of drug.

A preferred embodiment of this invention is directed to controlling the amount of drug migrating into the contact adhesive of a transdermal drug delivery device. By controlling the amount of drug which migrates from the drug reservoir into the contact adhesive, the initial loading dose of drug delivered can be effectively controlled in order to achieve a desired input of drug to saturate skin binding sites without requiring the drug to be directly preloaded into the adhesive.

A particularly preferred embodiment is directed to transdermal drug delivery devices for the administration of a drug at a substantially constant rate throughout an intended administration period wherein the drug reservoir contains drug at or in excess of saturation throughout the delivery period. According to this particularly preferred embodiment, the drug reservoir is initially provided with drug in excess of saturation and the adhesive and rate control membrane are initially drug-free. During heat equilibration the solubility of the drug in the reservoir and other layers increases from that at ambient conditions and the other layers will become saturated with the drug at this increased solubility level. After the heat equilibration process and cooling of the device to ambient conditions, the decrease in solubility of the other layers will cause precipitation of the drug in excess of saturation which will then remain in these other layers as a loading dose. The initial loading of drug in the reservoir is preferably selected so that the reservoir remains saturated with drug throughout the entire process.

Practice of this invention avoids the problems of preloading drug directly into the adhesive and provides an amount of drug in the adhesive greater than that possible from equilibration at normal conditions. Additionally, providing the drug reservoir and the contact adhesive each with drug at or in excess of saturation helps to prevent back flux of drug from the contact adhesive to the drug reservoir.

In accordance with the particularly preferred embodiment, the inventors have also discovered that testosterone may be effectively transdermally administered to hypogonadal males through non-scrotal skin with a lower incidence of skin irritation from a device of this invention comprising an amount of testosterone in excess of its saturation concentration in an ethanol carrier without additional permeation enhancers. Approximately 5–6 mg of testosterone may be transdermally delivered over 24 hours in order to achieve a mean serum testosterone concentration in hypogonadal males above the low end of the normal range for men (275–300 ng/dL) and a mean maximum testosterone concentration at the mid-normal range of about 500–600 ng/dL. This is contrary to the teachings of U.S. Pat. Nos. 5,152,997 and 5,164,990 which suggest the need to provide testosterone at a condition below saturation together with permeation enhancers in addition to ethanol in order to achieve effective testosterone concentrations by transdermal administration through non-scrotal skin. Furthermore, the ethanol and testosterone are provided in a single reservoir, thus simplifying the manufacture of the device.

Figure 1:
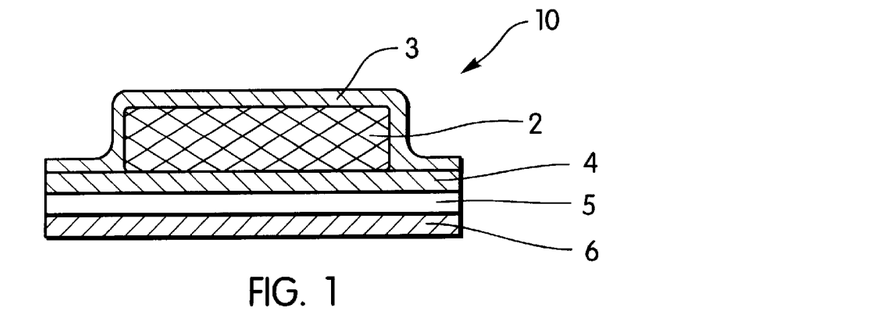
FIG. 1 is a cross-sectional view of one embodiment of the transdermal drug delivery system according to this invention.

Referring now to FIG. 1, a drug delivery device 10 comprising an aqueous gel reservoir 2 according to this invention is shown. Delivery device 10 comprises a backing member 3 which serves as a protective cover for the device, imparts structural support, and substantially keeps components in device 10 from escaping the device. Device 10 also includes reservoir 2, which contains the drug with or without a permeation enhancer, and bears on its surface distant from backing member 3, a rate-controlling membrane 4 for controlling the release of drug and/or permeation enhancer from device 10. The outer edges of backing member 3 overlay the edges of reservoir 2 and are joined along the perimeter with the outer edges of the rate-controlling membrane 4 in a fluid-tight arrangement. This sealed reservoir may be effected by pressure, fusion, adhesion, an adhesive applied to the edges, or other methods known in the art. In this manner, reservoir 2 is contained wholly between backing member 3 and rate-controlling membrane 4. On the skin-proximal side of rate-controlling membrane 4 are an adhesive layer 5 and a strippable liner 6 which would be removed prior to application of the device 10 to the skin.

According to the particularly preferred embodiment, the drug reservoir 2 is initially provided with a drug loading comprising an excess amount of drug beyond the saturation concentration of the drug in the reservoir such that, after heat equilibration according to this invention, the reservoir is maintained at a condition at or above saturation throughout a substantial portion of the predetermined drug administration period. This provides that the system will contain sufficient drug to provide the contact adhesive with the desired loading dose of drug during the heat equilibration and that the drug reservoir will contain sufficient drug in order to achieve the desired serum concentration levels for the intended period of administration. Additionally, maintaining the drug reservoir at or in excess of saturation provides for a substantially constant rate of administration.

Figure 2A:
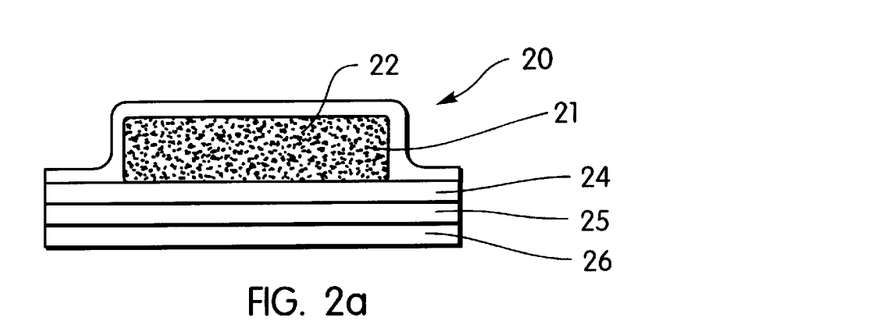
Figure 2B:
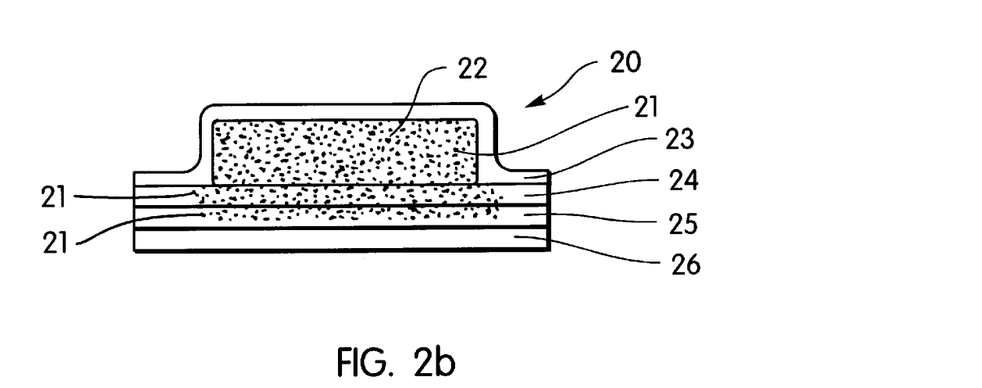
Figure 2C:
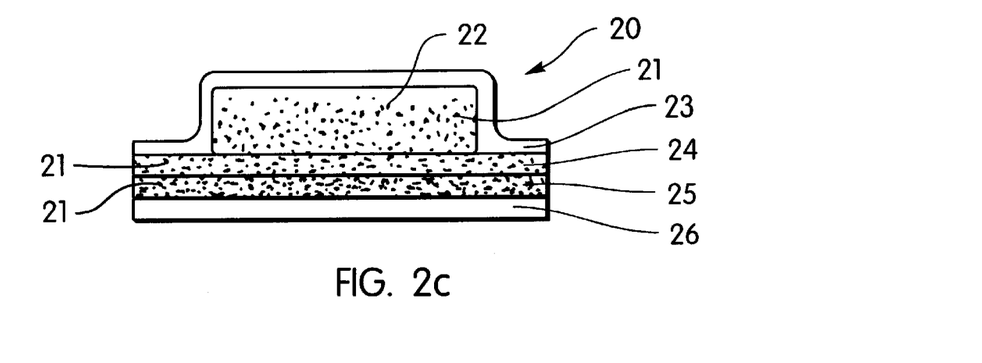

To effect the heat equilibration process of this invention according to this particularly preferred embodiment, the drug delivery device with the drug reservoir comprising drug in excess of saturation is subjected to an elevated temperature for a predetermined period of time. FIG. 2(a) depicts drug delivery device 20 with excess drug 21 in the drug reservoir 22 as it is provided prior to heat equilibration. The device 20 also comprises backing 23, rate control membrane 24, contact adhesive 25, and release liner 26. Upon heating the device 20 to the predetermined temperature the solubility of the drug in all of the layers increases. Therefore, as long as the drug reservoir layer remains saturated with drug during the predetermined time period, drug migrates from the drug reservoir into the adjoining layers 24 and 25 of the device at an accelerated rate due to the shift in equilibrium, as depicted in FIG. 2(b). The shift in equilibrium also allows for a greater amount of drug to migrate into the adjoining layers, such as the contact adhesive 25, due to the increased solubility of the drug in the adhesive at the elevated temperature. After the predetermined time period, the device is removed from the elevated temperature and allowed to cool to ambient conditions. As the temperature decreases, the solubility of the drug in the adhesive also decreases, leaving an amount of drug 21 in excess of saturation in the contact adhesive at ambient conditions, as depicted in FIG. 2(c).

The amount of drug present in the therapeutic drug delivery device and required to achieve an effective therapeutic result depends on many factors, such as the minimum necessary dosage of the drug of the particular indication being treated; the solubility and permeability of the carrier and adhesive layer; and the period of time for which the device will be fixed to the skin. The minimum amount of drug is determined by the requirement that sufficient quantities of drug must be present in the device to maintain the desired rate of release over the given period of application. The maximum amount for safety purposes is determined by the requirement that the quantity of drug present does not produce toxic effects. Generally, the maximum concentration is determined by the amount of drug that can be received in the carrier without producing adverse histological effects such as irritation, an unacceptably high initial loading dose of drug into the body, or adverse effects on the characteristics of the delivery device such as the loss of tackiness, viscosity, or deterioration of other properties.

The initial loading of drug in the carrier will determine the useful life of the device, typically from 8 hours to seven days. The invention can be used for such time periods, however, certain preferred embodiments are particularly adapted for administration periods of up to about 24 hours. As discussed with respect to the particularly preferred embodiment, the drug is initially present in the carrier at a concentration at or in excess of saturation. The drug may, however, be present at a level below saturation during use without departing from this invention as long as the drug is continuously administered to the skin or mucosal site in an amount and for a period of time sufficient to provide the desired therapeutic rate.

The backing may be a breathable or occlusive material including, but not limited to, polyethylene, polyurethane, polyester or ethylene vinyl acetate films. A polyethylene terephthlate/ethylene vinyl acetate backing is preferred. If an ethylene vinyl acetate is employed as the backing, preferably, it has a vinyl acetate content of 33% or 40%.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polypropylene, polyvinyl acetate, ethylene n-butyl acetate and ethylene vinyl acetate copolymers. The rate control membrane may also include an amount of mineral oil or other diffusive medium as disclosed in U.S. Pat. No. 3,797, 494, herein incorporated by reference in its entirety.

The reservoir formulation may be aqueous or non-aqueous based. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with the drug and the permeation-enhancing mixture, if used, in addition to any other components in the formulation.

When using a non-aqueous based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/ oil polymers containing from 4–25% high molecular weight polyisobutylene and 20–81% low molecular weight polyisobutylene with the balance being an oil such as mineral oil or polybutene may also be used as the matrix material.

Suitable adhesives are well known in the art and include, but are not limited to, silicone and/or acrylate polymers including mixtures and graft copolymers thereof, polyisobutylene (PIB) adhesives comprising mixtures of low and high molecular weight PIB's and an optional amount of mineral oil or polybutene, such as those described in U.S. Pat. No. 5,508,038, herein incorporated in its entirety by reference, styrene-butadiene copolymers, and styrene-isoprene copolymers with tackifier(s).

Although any drug which is suitable for transdermal administration can be delivered according to this invention, certain drugs are particularly suited for administration from devices according to this invention. Testosterone and its esters constitute a preferred drug for delivery according to this invention, particularly for use in the treatment of hypogonadic males. Other preferred drugs include hormones, particularly steroids, estrogens such as estradiol and its esters, anabolic agents such as nandrolone and its esters, progestogens such as progesterone and its esters, corticosteroids, and narcotic agents.

The surface area of the device of this invention can vary from about 5 cm$^2$ to about 75 cm$^2$. A typical device, however, will have a surface area within the range of about 20–60 cm$^2$. A typical transdermal device according to this invention is fabricated as an approximately 60 cm$^2$ generally elliptical or rectangular patch with rounded corners.

The drug delivery devices of this invention may also contain other permeation enhancers, stabilizers, dyes, diluents, pigments, carriers, inert fillers, antioxidants, excipients, gelling agents, anti-irritants, vasoconstrictors, as are known to the art.

The devices of this invention can be designed to effectively deliver drug for an extended period of time from several hours up to seven days or longer. Seven days is generally the maximum time limit for application of a single device because the adverse effect of occlusion of a skin site increases with time and a normal cycle of sloughing and replacement of the skin cells occurs in about seven days.

According to the particularly preferred embodiment for the transdermal administration of testosterone, the drug reservoir comprises 20–30 wt % testosterone, 68–80 wt % ethanol, and 1–2 wt % of a gelling agent such as hydroxypropyl cellulose, the rate control membrane comprises an ethylene vinyl acetate copolymer having a vinyl acetate content of 5–30 wt %, preferably 9–18%, and the adhesive comprises a polyisobutylene mixture comprising high molecular weight PIB/low molecular weight PIB/mineral oil in a ratio of 0.75–1.25/1–1.5/1.5–2.5, most preferably 1/1.25/2.

The aforementioned patents describe a wide variety of materials which can be used for fabricating the various layers and components of the drug delivery devices according to this invention. This invention, therefore, contemplates the use of materials other than those specifically disclosed herein, including those which may hereafter become known to the art and to be capable of performing the necessary functions.

The following examples are offered to illustrate the practice of the present invention and are not intended to limit the invention in any manner.

EXAMPLE 1

Transdermal delivery systems for the administration of testosterone through non-scrotal skin were made as follows. A reservoir gel comprising 26 wt. % testosterone, 1–2 wt. % hydroxypropyl cellulose, and the remainder 95% ethanol was prepared by mixing testosterone, 95% ethanol and adding hydroxypropyl cellulose with mixing. The gel loading was 21 mg testosterone/cm$^2$.

A contact adhesive composition was made by mixing polyisobutylene (MW 1200000), polyisobutylene (MW 35000) and light mineral oil in a weight ratio of 1:1.25:2. A 50 micron thick layer of the contact adhesive was cast onto a 75 micron thick film of siliconized polyethylene terephthalate release liner. The contact adhesive side of the resulting two layer subassembly was laminated to a 50 micron thick film of ethylene vinyl acetate (EVA) copolymer (9% vinyl acetate). The gelled testosterone-ethanol mixture was placed on the EVA membrane. A backing member comprised of aluminized polyethylene terephthalate with an EVA heat sealable coating was laid over the gels and heat-sealed to the EVA copolymer using a rotary heat seal machine. Finished systems were punched from laminate using a circular punch and placed in sealed pouches to prevent loss of volatile components.

Systems were then subjected to 35° C., 40° C., or 50° C. for a seven day period and release rates were tested at room temperature and compared with systems kept at room temperature for 1 month in order to observe the effect of temperature on the loading dose.

The release liner of the laminate was removed and the system was then mounted on a Teflon® rod. A known volume of receptor solution (0.10% phenol/H$_2$O) was then placed in a test tube and was equilibrated at 35° C. The Teflon rod with the attached system was then placed in a water bath at 35° C. Mixing was accomplished by attachment to a motor which caused constant vertical mixing.

At given time intervals, the entire receptor solution was removed from the test tubes and replaced with an equal volume of fresh receptor solutions previously equilibrated at 35° C. The receptor solutions were stored in capped vials at 4° C. until assayed for testosterone content by HPLC. From the drug concentration and the volume of the receptor solutions, the area of permeation and the time interval, the flux of the drug was calculated as follows: (drug concentration X volume of receptor)/(area x time)=flux ($\mu$g/cm$^2$•hr).

Figure 3:
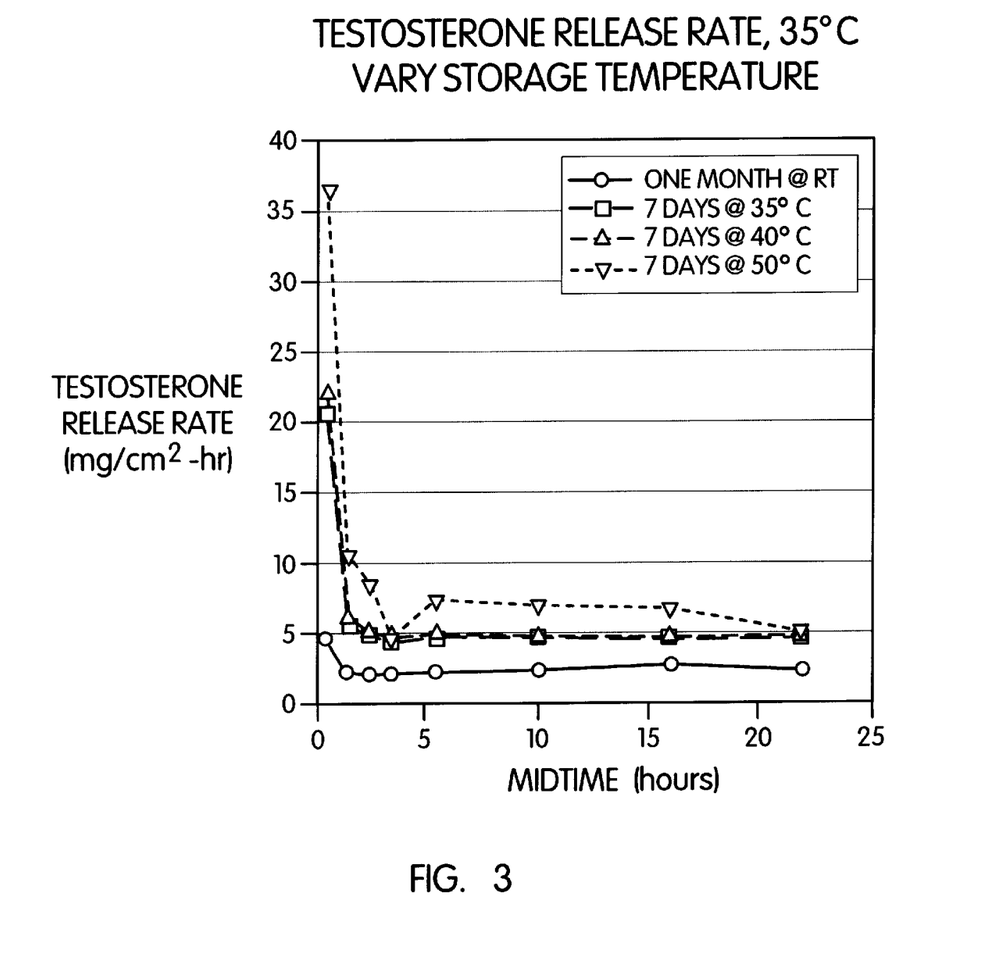
FIG. 3 depicts testosterone release rates from systems subjected to various heat equilibration procedures.

FIG. 3 shows the effect of heat equilibration on the testosterone release rate. From the results depicted in FIG. 3, it is seen that temperature demonstrated the most significant effect on testosterone release rate during the 0–2 hour initial delivery period, which corresponds to the delivery of the loading dose. The loading dose for this system corresponds approximately to the cumulative release of testosterone during the 0–2 hour period. The effect of heat equilibration on the loading dose, as measured by the cumulative release of testosterone during the 0–2 hour period, is shown in Table 1. As seen in Table 1, the loading dose increased with the temperature of the heat equilibration process.

TABLE 1

Effect of Heat Equilibration
On Loading Dose of Testosterone

| Group | 0–2 Hour Cumulative Release ($\mu$g/cm$^2$) |
|---|---|
| I | 6.7 |
| II | 26.0 |
| III | 28.2 |
| IV | 46.8 |

Group I was stored at room temperature for 1 month.
Group II was placed in oven at 35° C. for 7 days.
Group III was placed in oven at 40° C. for 7 days.
Group IV was placed in oven at 50° C. for 7 days.

EXAMPLE 2

Transdermal therapeutic systems comprising an aqueous ethanolic gel were prepared according to the following procedure. Fentanyl base was added to 95% ethanol and stirred to dissolve the drug. Purified water was then added to generate a mixture containing 14.7 mg/g of fentanyl in a 30% ethanol-water solvent. 2% of hydroxyethyl cellulose gelling agent was added slowly to the solution with stirring and mixed until a smooth gel was obtained (approximately 1 hour). A 0.05 mm thick contact adhesive layer was formed on a fluorocarbon-diacrylate treated polyester film which comprised the release liner for the system by solution casting an amine resistant silicone medical adhesive onto the polyester film from a solution in trichlortrifluorethane. A 0.05 mm thick rate controlling membrane comprised of EVA (9% VA) was pressure laminated to the exposed adhesive. A backing member comprised of a multilaminate of polyethylene, aluminum, polyester, and EVA was also provided and the aqueous gel pouched between the backing member and the release liner/adhesive/rate controlling membrane on a rotary heat-seal machine at a gel loading of 15 mg/cm$^2$. Sealed pouches in sizes of 10 cm$^2$ were die cut and immediately pouched to avoid loss of ethanol.

The effect of heat equilibration on 10 cm$^2$ systems prepared according to the above procedure was tested. Systems were subjected to various temperature/time regimens and thereafter kept at 25° C. The cumulative release of fentanyl during the initial 0–2 hour period was measured using the procedure set forth in Example 1 to test release rates. The release rates were measured after storage at 25° C. for two months. The results are shown in Table 2.

TABLE 2

Effect of Heat Equilibration on Fentanyl Loading Dose

| Group | 0–2 hr release (µg/hr) |
|---|---|
| I | 208.9 |
| II | 246.3 |
| III | 404.2 |
| IV | 445.1 |

Group I was placed in oven at 30° C. for 7 days before storage at 25° C.
Group II was placed in oven at 40° C. for 3 days before storage at 25° C.
Group III was placed in oven at 51° C. for 1 day before storage at 25° C.
Group IV was placed in oven at 60° C. for 1 day before storage at 25° C.

Table 2 shows that the cumulative release of drug during the initial 0–2 hour period of administration increases as the temperature of the heat equilibration process increases. This initial 0–2 hour delivery period corresponds approximately to the delivery of the loading dose. After 2 months storage at room temperature, no detectable movement of fentanyl back into the drug reservoir from the adhesive was observed. It is seen from Table 2 that the release of fentanyl during the 0–2 hour period (loading dose) increases with temperature of heat equilibration.

EXAMPLE 3

Figure 4:
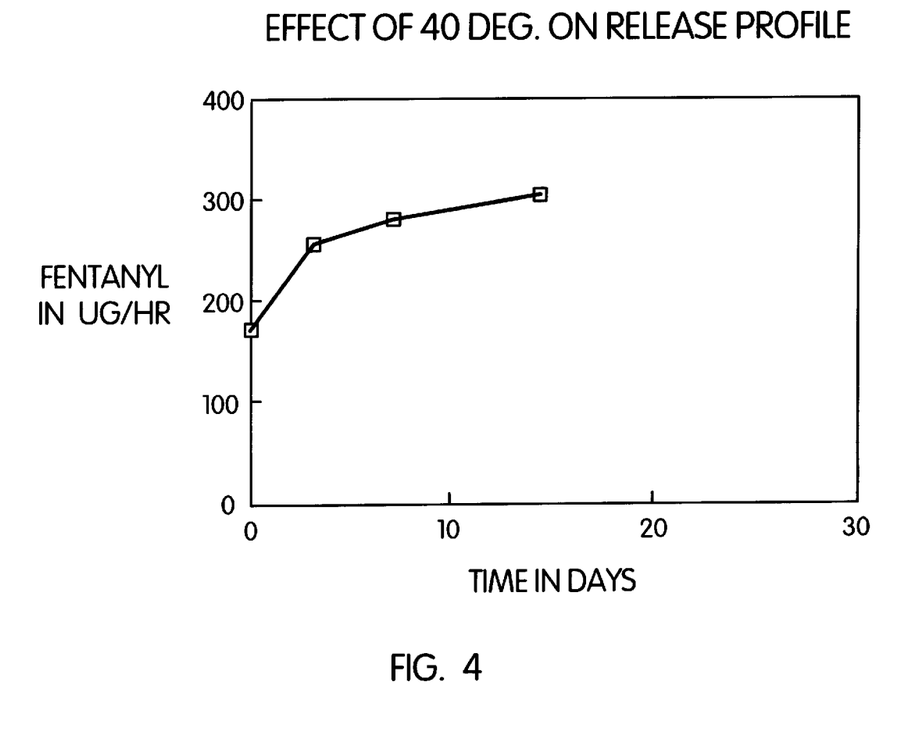
FIG. 4 depicts the effect of exposure time at 40° C. on the initial fentanyl release rate from a transdermal device.

The effect of exposure time at an elevated temperature heat equilibration process was investigated. Systems prepared according to Example 2 were kept at 40° C. and release rates were taken at 0, 3, 7, and 14 day intervals. FIG. 4 shows the effect of storage at 40° C. on the initial release of fentanyl during the 0–2 hour period (loading dose) after delivery is initiated. As seen in FIG. 4, the loading dose increased with time of exposure.

EXAMPLE 4

10 cm$^2$ systems were prepared according to Example 2. Some of these systems were subjected to 40° C. for four days, while the remaining systems were kept at room temperature. In vitro release profiles using the procedure set forth in Example 1 were determined for each set of systems. The average loading dose for these systems, measured by the 0–2 hour cumulative release, was determined to be 199.00 µg/hr for the room temperature systems and 282.25 µg/hr for the systems kept at 40° C. for four days. An amount of solid drug was observed in the drug reservoir gel of each set of systems before performing the release rate tests, indicating that the drug reservoir comprised an amount of drug in excess of saturation. Solid drug was observed in the drug reservoir gel of the heat equilibrated systems as they were removed from the oven.

Although the above examples have described the process as being performed on pouched systems it is also possible to perform this process prior to either system punching or pouching in those cases where there are no concerns about loss of volatile components.

The invention has been described in detail with particular reference to certain preferred embodiments thereof, but it will be understood that variations and modifications can be affected within the scope and spirit of the

What is claimed is:

1. A device for the transdermal administration of testosterone through intact, non-scrotal skin over an administration period comprising:

a) a backing layer;

b) a drug reservoir comprising a carrier and testosterone dispersed in excess of saturation within the carrier;

c) a contact adhesive on the skin proximal side of the drug reservoir for maintaining the device in testosterone-transmitting relation with intact, non-scrotal skin, wherein the contact adhesive further comprises testosterone dispersed in excess of saturation within the contact adhesive at the beginning of the administration period, wherein said excess in the drug reservoir is sufficient to maintain testosterone at a level at or in excess of saturation in the drug reservoir throughout a substantial portion of the administration period.

2. A device according to claim 1 further comprising a rate control membrane on the skin proximal side of the drug reservoir.

3. A device according to claim 1 wherein the carrier comprises an aqueous gel.

4. A device according to claim 3 wherein the carrier comprises ethanol.

5. A device according to claim 2 wherein the rate control membrane comprises an ethylene vinyl acetate copolymer having a vinyl acetate content of 5–30%.

6. A device according to claim 5 wherein the vinyl acetate content is 9–18%.

7. A device according to claim 1 wherein the adhesive comprises a blend of low molecular weight polyisobutylene and high molecular weight polyisobutylene.

8. A device according to claim 7 wherein the ratio of low molecular weight polyisobutylene to high molecular weight polyisobutylene is 1.25:1.

* * * * *